United States Patent [19]
Hall

[11] 4,447,916
[45] May 15, 1984

[54] MECHANICAL KNEE
[76] Inventor: Thomas D. Hall, 821 Hudson Rd., Glenview, Ill. 60025
[21] Appl. No.: 294,471
[22] Filed: Aug. 20, 1981
[51] Int. Cl.³ .............................................. A61F 1/04
[52] U.S. Cl. ............................................. 3/22; 3/27
[58] Field of Search .................... 3/22, 26, 4, 6, 27, 3/28, 33, 34, 35, 2

[56] References Cited
U.S. PATENT DOCUMENTS

| | | | |
|---|---|---|---|
| 49,528 | 8/1865 | Jewett | 3/29 X |
| 1,283,093 | 10/1918 | Critchley | 3/24 |
| 1,334,834 | 3/1920 | Blatehford | 3/26 |
| 1,383,365 | 7/1921 | Worman | 3/35 X |
| 1,390,915 | 9/1921 | Leth | 3/22 |
| 2,770,811 | 11/1956 | Steeper | 3/22 |
| 3,030,634 | 4/1962 | Bair | 3/22 |

FOREIGN PATENT DOCUMENTS

| | | | |
|---|---|---|---|
| 649490 | 8/1937 | Fed. Rep. of Germany | 3/22 |
| 2056281 | 3/1981 | United Kingdom | 3/27 |

Primary Examiner—Richard J. Apley
Assistant Examiner—David J. Isabella

[57] ABSTRACT

A mechanical knee converts the weight of the wearer to a knee extensor force. A rotatable pulley is supported by the lower leg, and a collar which is attached to the upper leg is connected to the pulley by a link. The link is eccentrically connected to the pulley, and when the user applies weight to the collar, the link rotates the pulley. The extensor force is applied to the collar and the upper leg by a bar which is attached to the leg and which is slidably connected to the pulley by a sleeve.

9 Claims, 11 Drawing Figures

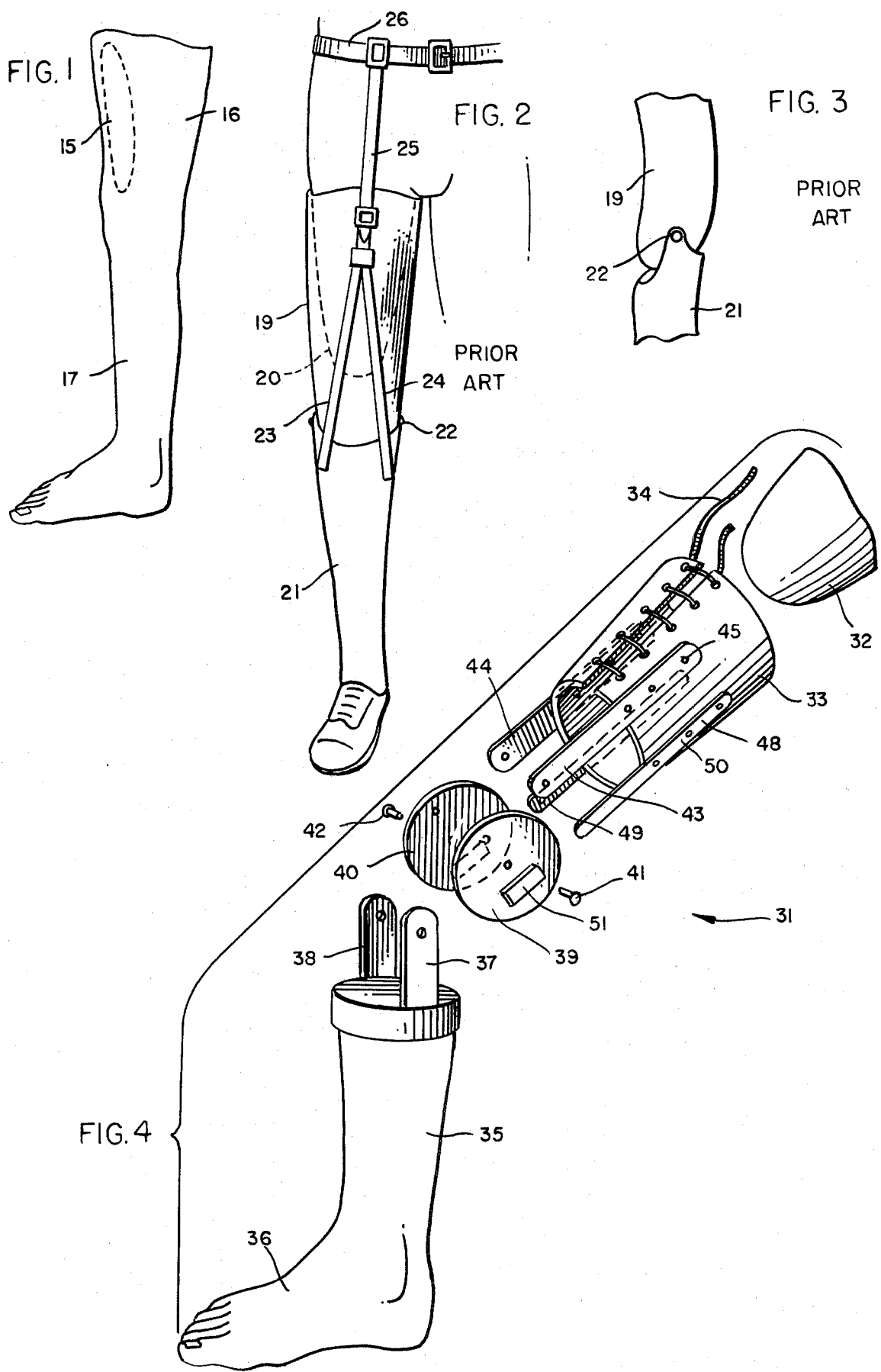

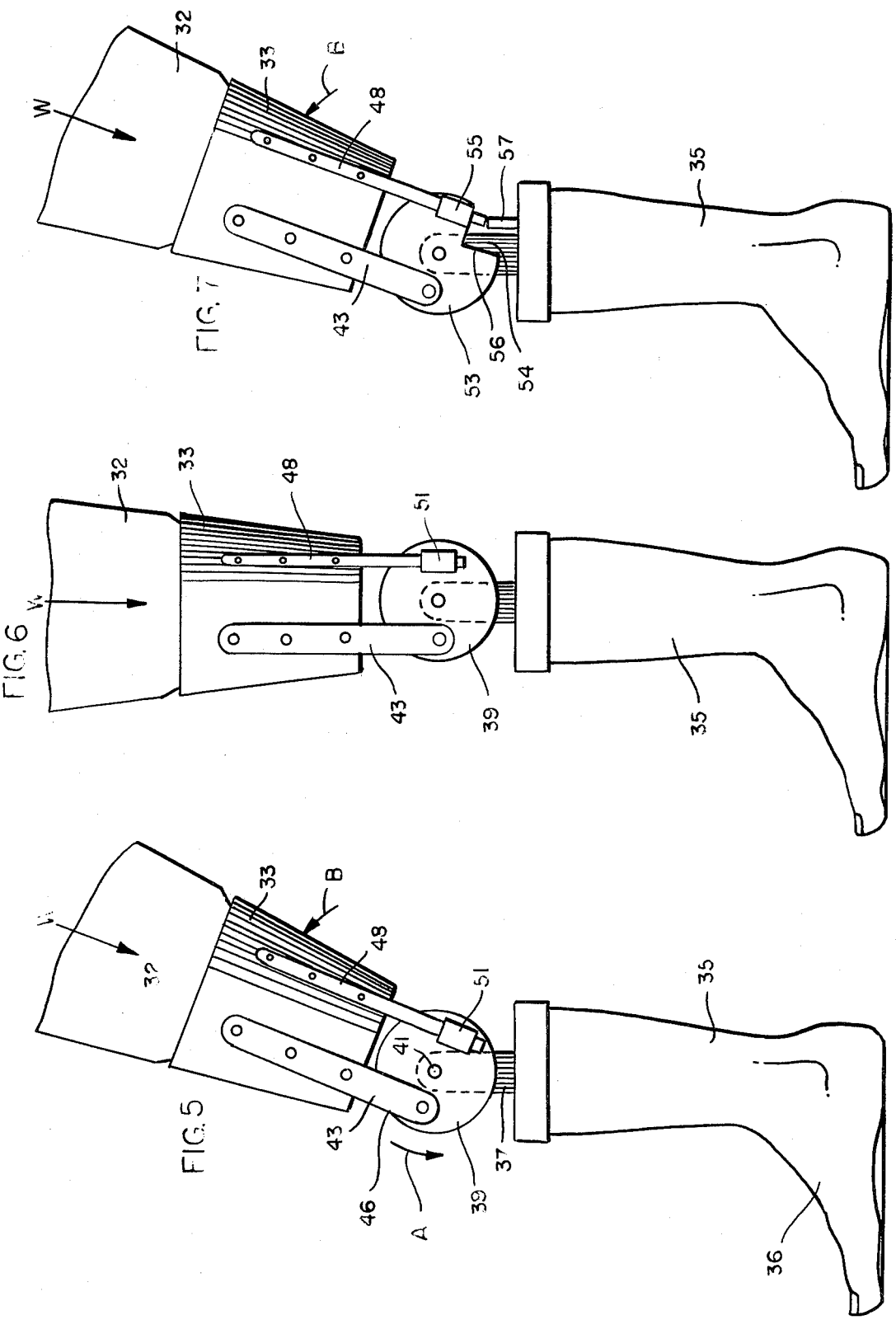

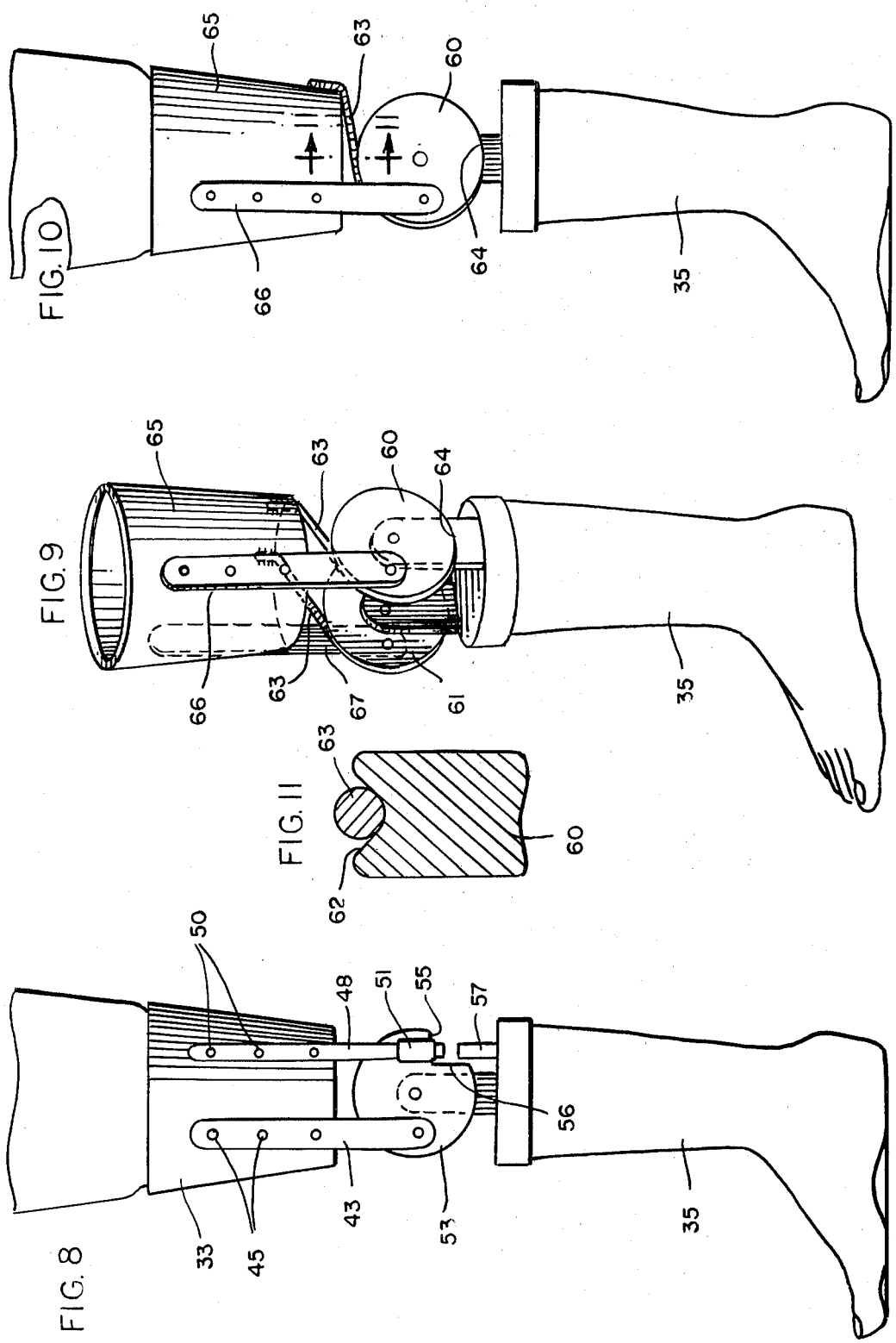

MECHANICAL KNEE

BACKGROUND AND SUMMARY

This invention relates to a mechanical knee for converting the weight of the wearer to a knee extensor force.

Recent studies on the biomechanics of the knee have revealed new insights regarding the extension mechanism. The role of the patella as a pulley mechanism has never been fully clarified. However, the study of muscle activity in the thigh muscles has revealed that the real function of the musculature is to elevate the thigh with the body weight over the planted lower extremity rather than just to extend the knee during the swing phase of gait. In addition the musculature prevents the collapse of the flexed knee during weight bearing.

With existing prosthetic legs extension is obtained by utilization of centrifugal force when the patient swings the leg forward before weight bearing. This extension may be assisted by an elastic strap on the front of the prosthesis. With this prosthesis, extension must be obtained before weight is applied.

The invention provides a mechanical knee for use with either a prosthetic lower leg or with a leg brace. The mechanical knee utilizes a pulley and an eccentric connection between the pulley and the upper leg to convert the weight of the wearer to a rotational force on the pulley. The rotational force of the pulley acts on a bar which extends between the pulley and the upper leg and creates an extensor force on the upper leg. The mechanical knee converts weight bearing to a knee extensor force without having to swing the lower leg.

DESCRIPTION OF THE DRAWING

The invention will be explained in conjunction with illustrative embodiments shown in the accompanying drawing, in which:

FIG. 1 is a perspective view of a human leg showing the quadriceps muscle;

FIG. 2 is a perspective view of a prior art prosthetic leg;

FIG. 3 is a fragmentary side elevational view of the prosthetic leg of FIG. 2;

FIG. 4 is an exploded perspective view of a mechanical knee and lower leg prosthesis formed in accordance with the invention;

FIG. 5 is a side elevational view showing the operation of the mechanical knee and prosthetic lower leg as weight is applied to the flexed knee;

FIG. 6 is a side elevational view showing the mechanical knee in its extended position;

FIG. 7 is a view similar to FIG. 5 showing another embodiment of the mechanical knee which is provided with a stop for preventing excessive rotation of the pulleys;

FIG. 8 shows the mechanical knee of FIG. 7 in its extended position;

FIG. 9 is a perspective view of a different embodiment of the mechanical knee;

FIG. 10 is a side elevational view of the mechanical knee of FIG. 9; and

FIG. 11 is an enlarged fragmentary sectional view taken along the line 11—11 of FIG. 10.

DESCRIPTION OF SPECIFIC EMBODIMENTS

FIG. 1 illustrates a normal leg. The quadriceps muscle 15 in the upper leg 16 extends the lower leg 17 during walking and prevents collapse of the knee when weight is placed on the leg when it is flexed. Ligaments extend over the patella or knee cap, and the quadricep muscles pull these ligaments to extend the knee.

A person whose quadricep muscles are paralyzed must either walk with a goosestep gait and bear weight with the leg completely straight or have a brace which is locked in the extended position. A person whose leg is amputated above the knee has no knee for the quadricep muscles to work on. Prosthetic legs are available for above-knee amputees, but before the amputee can step on the prosthetic leg, he must swing the upper leg in order to straighten the knee before he can put weight on the leg.

FIGS. 2 and 3 illustrate a conventional prior art prosthetic leg 18 worn by an above-knee amputee. The prosthetic leg includes a socket 19 which encompasses and supports the upper leg stump 20. A lower prosthetic leg 21 is hingedly connected to the upper socket by hinge pins 22. Elastic straps 23 and 24 are attached to the prosthetic lower leg 21 and to a suspension strap 25 above the knee. The suspension strap is attached to a belt 26. Some above-knee prostheses also have a pelvic band which extends around the pelvis of the wearer to hold up and to steady the prosthesis with regard to rotation.

The amputee operates the prosthesis shown in FIGS. 2 and 3 by swinging his leg forward so that centifugal force extends or straightens the lower leg 21 with respect to the upper leg or thigh. The elastic straps 23 and 24 assist in extending the lower leg. The leg must be completely straight before the amputee puts weight on it, or it will collapse. A prosthetic leg may also be equipped with a hydraulic mechanism that slows down flexion so that the knee can bend during walking and weight bearing without collapsing until the weight can be transferred to the other leg.

FIG. 4 illustrates a prosthetic leg 31 which includes a mechanical knee made in accordance with my invention. The prosthetic leg is intended for use with an above-knee amputation. The stump 32 of the amputated upper leg fits into a corset or collar 33 or other socket-providing device, and the collar can be tightened by laces 34.

A prosthetic lower leg 35 includes a foot portion 36, and a pair of support brackets 37 and 38 extend upwardly from the top of the lower leg. Pulleys 39 and 40 are rotatably mounted on the brackets by pins or axles 41 and 42, which extend through openings in the brackets. The two pulleys rotate on a common axis, and this axis is located at the point of knee rotation before amputation.

A pair of links 43 and 44 are attached to the collar 33, as by rivets 45, and each link is pivotally connected to one of the pulleys eccentrically of the axis of rotation. Referring to FIG. 5, the link 43 is attached to the pulley 39 by pin 46.

A pair of extensor bars 48 and 49 are also attached to the collar, as by rivets 50. Each extensor bar is connected to one of the pulleys so that the extensor bar can reciprocate with respect to the pulley in a direction which is generally perpendicular to the axis of rotation. However, rotation of the pulley will rotate the extensor bar. The particular connecting means illustrated in the drawings is a sleeve or tube 51 which is attached to each pulley eccentrically with respect to the axis and on the other side of the axis from the link 43 or 44. The extensor bars can slide within the sleeves, but translation of the sleeves which is caused by rotation of the pulleys will cause a corresponding translation of the extensor bars.

FIG. 5 illustrates the prosthesis as the wearer places some of his weight, indicated by the force vector W, on the collar 33 during walking. The prosthetic leg is in a position which corresponds to the position of a natural leg when the knee is flexed during walking. The foot portion of the prosthetic lower leg is planted on the ground, and the longitudinal axis of the collar and the amputated upper leg extend at an angle with respect to the vertical. The force of the body weight is transmitted through the collar to the two links 43 and 44, and the links urge the pulleys 39 and 40 to rotate in a counter-clockwise direction as indicated by the arrow A. The bars 48 and 49 are also urged to move in the direction of the force W, but the bars slide within the sleeves 51 on the pulleys and therefore do not apply a rotating force to the pulleys.

Counterclockwise rotation of the pulleys causes the sleeves 50 to be translated, i.e., to rotate or travel with the pulley in an arch. Since the sleeves are fixed on the pulleys, the translation of the sleeve will apply forces on the bars 48 and 49 which will swing the bars in a counter-clockwise direction as indicated by the arrow B. The collar 33 and the upper leg are thereby forced into a vertical position as illustrated in FIG. 6, which corresponds to the position of a natural leg when the knee is extended. The full weight of the wearer can then be transmitted vertically through the mechanical knee to the prosthetic lower leg, and the wearer can lift his other leg and take another step. A lever-type mechanical advantage can be obtained by making the distance between the pulley axis 41 and the pin 46 for the link 43 greater than the distance between the pulley axis and the sleeve 50. The ratio of the rotating force applied to the pulley by the link and the rotating force applied by the pulley to the bar 48 through the sleeve 50 will be approximately equal to the ratio of the distance between the pulley axis and the sleeve and the distance between the pulley axis and the pivot pin 46.

Although I have described the rotating parts 39 and 40 of the mechanical knee as pulleys or wheels, these parts need not have the shape of a conventional pulley or wheel. The term "pulley" is intended to include any device which rotates and to which a force-transmitting member from the upper leg can be attached eccentrically.

FIGS. 7 and 8 illustrate a modified mechanical knee in which each pulley 53 is provided with a pie-shaped recess 54 which provides a pair of flat stop surfaces 55 and 56. A pair of stop posts 57 extend upwardly from the top of the prosthetic lower leg 35 for limiting the rotation of the two pulleys. In FIG. 7 the stop surfaces 55 engage the stop posts, and the prosthetic leg cannot be flexed beyond the position illustrated in FIG. 7. FIG. 8 shows the prosthetic leg after body weight has been applied to swing the upper leg into an extended position relative to the lower prosthetic leg. In this position the stop surfaces 56 engage the stop posts and prevent hyperextension. The stop posts are advantageously cushioned by rubber or the like to reduce shock as the stop surfaces of the pulleys engage the posts. Since stance flexion of the natural knee is only about 20° at most, the pulleys need to rotate only about 20° to provide adequate flexion.

FIGS. 9 and 10 illustrate another embodiment of the mechanical knee. The pulleys 60 and 61 have a track or groove 62 (FIG. 11) in their outer peripheries. A cable 63 is attached to each pulley within the groove (as by a pin 64) and extends around a portion of the pulley. The other end of each cable is attached to the posterior of the socket-providing collar or corset 65. Links 66 and 67 are eccentrically connected to the pulleys 60 and 61 and are rigidly attached to the collar 65 by a plurality of rivets or fastening pins.

When the mechanical knee shown in FIGS. 9 and 10 is in a flexed position corresponding to the positions illustrated in FIGS. 5 and 7 and weight is applied to the collar 65 by the upper leg, the forces transmitted by the links 66 and 67 to the pulleys cause the pulleys to rotate counter-clockwise. Counterclockwise rotation of the pulleys will pull the upper ends of the cables 63 and will swing the collar 65 and the upper leg into an upright or extended position as shown in FIG. 10.

Although I have described my mechanical knee in conjunction with a prosthetic leg for an above-knee amputee, the mechanical knee can also be used with a brace which fits on a natural leg to provide an extensor force for a person whose quadriceps muscle is paralyzed. The pulleys would be rotatably mounted on each side of the knee by a portion of the brace which is attached to the lower leg, and the extensor-force transmitting links which are eccentrically connected to the pulleys would be attached to a portion of the brace which is attached to the upper leg.

While in the foregoing specification a detailed description of specific embodiments of the invention was set forth for the purpose of illustration, it will be understood that many of the details hereingiven may be varied considerably by those skilled in the art without departing from the spirit and scope of the invention.

I claim:

1. A mechanical knee for extending the upper leg of a user with respect to the lower leg of the user comprising a pulley adapted to be rotatably supported by the lower leg, a collar for attachment to the upper leg, a link attached to the collar and pivotably attached directly to the pulley eccentrically with respect to the axis of rotation of the pulley and extensor means extending between the pulley and the collar for rotating the collar into an extended position with respect to the lower leg when the pulley is rotated by weight applied to the collar and the link.

2. The mechanical knee of claim 1 including a second pulley adapted to be rotatably supported by the lower leg, a second link attached to the collar and pivotally attached to the second pulley eccentrically with respect to the axis of rotation of the second pulley, and second extensor means extending between the second pulley and the collar for rotating the collar into an extended position with respect to the lower leg when the second pulley is rotated by weight applied to the collar and the second link.

3. The mechanical knee of claim 1 in which the extensor means comprises a bar attached to the collar and a sleeve attached to the pulley, the bar extending slidably into the sleeve whereby the bar can move within the sleeve in a direction generally perpendicular to the axis of rotation of the pulley but rotation of the pulley and the sleeve will rotate the bar and the collar.

4. The mechanical knee of claim 1 in which the extensor means comprises a cable extending around a portion of the periphery of the pulley, one end of the cable being attached to the pulley and the other end of the cable being attached to the collar whereby rotation of the pulley with respect to the lower leg will rotate the collar.

5. The mechanical knee of claim 1 including a prosthetic lower leg having a lower foot portion and an upper end, said pulley being rotatably mounted on the upper end of the prosthetic lower leg.

6. The mechanical knee of claim 5 including stop means mounted on the upper end of the prosthetic lower leg for engaging a portion of the pulley and for preventing further rotation of the pulley when the collar reaches the extended position with respect to the lower leg.

7. The mechanical knee of claim 6 in which the pulley is provided with a recess which has a stop surface which extends generally parallel to the axis of the socket, said stop surface engaging the stop means when the collar reaches the extended position with respect to the lower leg.

8. A prosthesis for an above-knee amputee comprising;
(a) a prosthetic lower leg having a lower foot portion and an upper end,
(b) a pair of pulleys rotatably mounted on the upper end of the prosthetic lower leg for rotation about a common axis,
(c) a socket for receiving and supporting the upper leg of the amputee,
(d) a pair of links attached to the socket, each of the links being pivotally attached directed to one of the pulleys eccentrically with respect to the axis of rotation of the pulleys,
(e) first extensor means extending between the socket and one of the pulleys for rotating the collar into an extended position with respect to the prosthetic lower leg when the pulley is rotated by weight applied to the socket and the links, and
(f) second extensor means extending between the socket and the other of the pulleys for rotating the collar into an extended position with respect to the prosthetic lower leg when the pulley is rotated by weight applied to the socket and the links.

9. The mechanical knee of claim 8 in which each of the first and second extensor means comprises a bar attached to the socket and a sleeve attached to one of the pulleys, each bar extending slidably into one of the sleeves whereby each bar can move within the sleeve in a direction generally perpendicular to the axis of rotation but rotation of the pulley and the sleeve will rotate the bar and the socket.

* * * * *